(12) United States Patent
Yoshioka et al.

(10) Patent No.: US 11,090,318 B2
(45) Date of Patent: Aug. 17, 2021

(54) WOUND HEALING PROMOTER

(71) Applicants: NAHLS CORPORATION CO., LTD., Kyoto (JP); NIHON UNIVERSITY, Tokyo (JP); RIKEN, Wako (JP)

(72) Inventors: Ryuzo Yoshioka, Osaka (JP); Yoko Tanaka, Tokyo (JP); Manabu Yaguchi, Tokyo (JP); Takashi Tanaka, Saitama (JP)

(73) Assignees: NAHIS CORPORATION CO., LTD., Kyoto (JP); NIHON UNIVERSITY, Tokyo (JP); RIKEN, Wako (JP)

( * ) Notice: Subject to any disclaimer, the term of this patent is extended or adjusted under 35 U.S.C. 154(b) by 65 days.

(21) Appl. No.: 16/605,625

(22) PCT Filed: Apr. 13, 2018

(86) PCT No.: PCT/JP2018/015607
§ 371 (c)(1),
(2) Date: Oct. 16, 2019

(87) PCT Pub. No.: WO2018/194000
PCT Pub. Date: Oct. 25, 2018

(65) Prior Publication Data
US 2020/0121700 A1    Apr. 23, 2020

(30) Foreign Application Priority Data
Apr. 17, 2017   (JP) .............. JP2017-081239

(51) Int. Cl.
*A61K 31/662*   (2006.01)
*A61P 1/02*   (2006.01)

(52) U.S. Cl.
CPC .............. *A61K 31/662* (2013.01); *A61P 1/02* (2018.01)

(58) Field of Classification Search
CPC ........... A61K 31/662; C07F 9/28; A61P 17/02
USPC ........................... 514/109; 558/70
See application file for complete search history.

(56) References Cited

U.S. PATENT DOCUMENTS

| 7,960,363 | B2 | 6/2011 | Tanaka et al. |
| 9,629,823 | B2 | 4/2017 | Kojima et al. |
| 2010/0280095 | A1 | 11/2010 | Tanaka et al. |
| 2016/0175280 | A1 | 6/2016 | Kojima et al. |

FOREIGN PATENT DOCUMENTS

| JP | 2010-280651 A | 12/2010 |
| JP | 2011-001387 A | 1/2011 |
| JP | 2012-062266 A | 3/2012 |
| JP | 2015-013828 A | 1/2015 |
| JP | 2016-011262 A | 1/2016 |
| JP | 2016-155762 A | 9/2016 |
| WO | 2010/123102 A1 | 10/2010 |

OTHER PUBLICATIONS

Fuziwara et al.: NMDA-type glutamate receptor is associated with cutaneous barrier homeostasis. Journal of Invest. dermat., vol. 120 (6), pp. 1023-1029, 2003.*
Hideaki Sumiyoshi et al., "Contribution of collagen subtypes to fibrillogenesis and fibrosis," Journal of clinical and experimental medicine, 2013, pp. 515-520, vol. 244, No. 6.
Gillian S. Ashcroft et al., "Mice lacking Smad3 show accelerated wound healing and an impaired local inflammatory response," Nature Cell Biology, Sep. 1999, pp. 260-266, vol. 1.
Vincent Falanga, MD et al., "Full-thickness wounding of the mouse tail as a model for delayed wound healing: accelerated wound closure in Smad3 knock-out mice," Wound Repair and Regeneration, 2004, pp. 320-326, vol. 12, No. 3.
(Continued)

*Primary Examiner* — Charanjit Aulakh
(74) *Attorney, Agent, or Firm* — Sughrue Mion, PLLC (57) ABSTRACT

A pharmaceutical preparation efficaciously promotes tissue wound repair. The wound repair promoter according to the present invention includes at least one active ingredient selected from the group consisting of compounds represented by Formula (1), salts of the compounds, and hydrates of the compounds or the salts. In the formula, $R^1$ and $R^2$ are each, identically or differently, selected from hydrogen and a hydrocarbon group optionally having one or more substituents selected from the group consisting of halogens, —$COOR^3$, —$CONR^3_2$, —$COR^3$, —CN, —$NO_2$, —$NHCOR^3$, —$OR^3$, —$SR^3$, —$OCOR^3$, —$SO_3R^3$, and —$SO_2NR^3_2$, where $R^3$ is, identically or differently in each occurrence, selected from hydrogen and an optionally substituted aliphatic hydrocarbon group; and n represents an integer of 1 or more.

[Chem. 1]

$$H_2N-\underset{\underset{COOH}{|}}{CH}-(CH_2)_n-\underset{\underset{O}{\|}}{P}\begin{matrix}OR^1\\OR^2\end{matrix}\qquad(1)$$

3 Claims, 4 Drawing Sheets

(56) References Cited

OTHER PUBLICATIONS

Yu Wang et al., "Smad3 null mice display more rapid wound closure and reduced scar formation after a stab wound to the cerebral cortex," Experimental Neurology, 2007, pp. 168-184, vol. 203.
Xiao-Jing Wang et al., "Role of TGF β-Mediated Inflammation in Cutaneous Wound Healing," Journal of Investigative Dermatology Symposium Proceedings, 2006, pp. 112-117, vol. 11.
Takashi Tanaka et al., "SLIM Is a Nuclear Ubiquitin E3 Ligase that Negatively Regulates STAT Signaling," Immunity, Jun. 2005, pp. 729-736, vol. 22.
International Search Report of PCT/JP2018/015607 dated Jul. 17, 2018.
Extended European Search Report dated Nov. 23, 2020, from the European Patent Office in European Application No. 18788419.2.
Fuziwara et al., "NMDA Glutamate Receptor Is Associated with Cutaneous Barrier Homeostasis", The Journal of Investigative Dermatology, vol. 120, No. 6. 2003, pp. 1023-1029 (7 Pages Total).
Jiang et al., "GGsTOP increases migration of human periodontal ligament cells in vitro via reactive oxygen species pathway", Molecular Medicine Reports, vol. 13, 2016, pp. 3813-3820 (8 pages total).
Lombardi et al., "Glutamate receptor antagonists protect against ischemia-induced retinal damage", European Journal of Pharmacology, vol. 271, 1994, pp. 489-495( 7 Pages total).
Fix et al., "Neonatal exposure to D, L-2-amino-3-phosphonopropionate (D,L-AP3) Produces lesions in the eye and optic nerve of adult rats", Developmental Brain Research, vol. 75, 1993, pp. 223-233(11 Pages Total).
Cordeiro et al., "Modulating conjunctival wound healing", Eye, vol. 14, 2000, pp. 536-547( 12 Pages Total).

\* cited by examiner

WOUND HEALING PROMOTER

TECHNICAL FIELD

The present invention relates to pharmaceutical preparations effective for promoting repair of tissue wounds. This application is a National Stage of International Application No. PCT/JP2018/015607 filed Apr. 13, 2018, which claims priority to Japanese Patent Application No. 2017-081239, filed Apr. 17, 2017 in Japan, the entire contents of which are incorporated herein by reference.

BACKGROUND ART

In an aging society, how to curb growth in medical spending is a great issue for the national finance. As a solution to solve the issue, preemptive medicine, which is a medical care to reduce or delay the onset of diseases, is needed more and more.

For example, a "periodontal disease" is a generic name for various pathoses caused by lipopolysaccharides (LPSs) in periodontal tissues (tissues that surround and support each tooth), where LPSs constitute the outer membranes of periodontal disease bacteria. The periodontal disease advances through gingivitis, periodontitis, and resorption of the alveolar bone, leads to tooth loss, and is indicated not only to cause impaired eating behaviors, but also to relate to diabetes, hepatitis, arteriosclerosis leading to myocardial infarction, chronic renal diseases, and aspiration pneumonia. Prophylaxis or treatment of the periodontal disease may significantly contribute to the prophylaxis of the above diseases.

One known, effective way to prevent such periodontal diseases is cleaning of the tooth surface to eliminate periodontal pathogenic microorganisms and to remove dental plaque and calculi, which serve as an incubator of the pathogenic microorganisms. When a subject has lowered biological functions due to aging or another cause, the cleaning of the tooth surface alone may fail to prevent the onset of periodontal diseases. No other way than surgery is known to recovery the periodontal tissues.

Patent Literature (PTL) 1 describes that a composition including a specific surfactant that inhibits LPS activity, when used as a dentifrice, can reduce or inhibit periodontal diseases. Unfortunately, this composition fails to repair a periodontal tissue once lost.

The term "wound" refers to a state in which the surface of a tissue is lost due to any cause such as an abrasion, laceration, incised wound, contusion, ulcer, bedsore, diabetic ulcer, thermal injury, inflammation, or necrotic cell death. Wound repair (wound healing) is one of most organized immunoreactions or inflammatory responses and is broadly divided into three stages or phases, (1) an inflammation phase, (2) a granulation tissue formation phase, and (3) a remodeling phase. In the inflammation phase, a tissue damage induces a local inflammatory response to cause neutrophils and macrophages to migrate to the wound site. The macrophages secrete various inflammatory cytokines and chemokines to further enhance the inflammatory response. In the granulation tissue formation phase subsequent to the inflammation phase, vascular endothelial cells grow to induce angiogenesis, and fibroblasts infiltrated into the wound site produce an extracellular matrix such as collagen, to form a granulation tissue. This leads to tissue regeneration. The fibroblasts in the granulation tissue differentiate into myofibroblasts, which contain a large amount of actin and have excellent contractility. The myofibroblasts act as a main cause of a wound contraction phenomenon, which occurs in this phase. This wound contraction is a useful process to efficiently reduce the wound area. In the remodeling phase, an upper part of the granulation tissue induces formation of epithelial cells, to remodel or rebuild an original, normal structure.

A past research indicates that transforming growth factor-$\beta$ (TGF-$\beta$) is a cytokine that plays a most significant role during the wound repair progress; that TGF-$\beta$, when binding to a receptor, transduces a signal via Smads; and that the TGF$\beta$/Smad signaling exactly regulates a wound healing-related gene (Non Patent Literature (NPL) 1). The term "regulation", however, includes both acceleration and deceleration, which are activities in opposite directions. Practically, mere acceleration of the TGF-$\beta$/Smad signaling does not mean increase in wound repair response. For example, as one known role of Smads in wound healing, Smad3 deficiency accelerates wound healing, indicating that lack of signaling by TGF-$\beta$ accelerates wound repair (NPL 2 and NPL 3). Another report mentions that transgenic mice over-expressing TGF-$\beta$1 exhibited a delay in wound healing, indicating that TGF-$\beta$1 has a negative activity on wound healing (NPL 4).

PDZ and LIM domain protein-2 (PDLIM2) is an intranuclear ubiquitin ligase belonging to the LIM protein family and has PDZ and LIM domains. PDLIM2 intranuclearly combines with, ubiquitinates, and decomposes signal transducer and activator of transcription 4 (STAT4), which is one of essential transcription factors for differentiation of T cells into T helper subset 1 (Th1) cells. Thus, PDLIM2 terminates STAT4 signaling (NPL 5). PTL 2 mentions that silencing of PDLIM2 promotes skin deficiency repair.

Various cell growth factors have been proved to play significant roles in the wound healing process (wound repair process) and are expected to be efficacious in the treatment of skin wounds. Of members of the fibroblast growth factor (FGF) family, human basic fibroblast growth factor-2 (FGF2; also called "bFGF") has been found as a protein that is effective to significantly promote fibroblast growth and to promote angiogenesis. FGF2 is used as a therapeutic agent for intractable wounds such as bedsore and cutaneous ulcer.

CITATION LIST

Patent Literature

PTL 1: Japanese Unexamined Patent Application Publication (JP-A) No. 2011-1387
PTL 2: JP-A No. 2010-280651

Non Patent Literature

NPL 1: Ashcroft G S et al., Nat Cell Biol, 1, p 260 (1999)
NPL 2: Falanga V et al., Wound Repair and Regeneration, 12, p 320 (2004)
NPL 3: Wang Y, et al., Experimental Neurology, 203, p 168 (2007)
NPL 4: Wang X et al., J Investig Dermatol Symp Proc, 11, p 112 (2006)
NPL 5: Tanaka et al., Immunity, 22, p 729 (2005)

SUMMARY OF INVENTION

Technical Problem

Accordingly, the present invention has an object to provide a pharmaceutical preparation efficacious in promoting tissue wound repair.

The present invention has another object to provide a pharmaceutical preparation efficacious in promoting mucosal wound repair.

The present invention has still another object to provide a pharmaceutical preparation efficacious in promoting wound repair in a tissue including fibroblasts.

The present invention has still another object to provide a pharmaceutical preparation acting to prevent or reduce periodontal tissue loss caused by periodontal diseases and to repair or remodel such a periodontal tissue lost by periodontal diseases.

Solution to Problem

After intensive investigations to achieve the objects, the inventors of the present invention have found that a compound represented by Formula (1), when applied to fibroblasts undergoing an inflammatory response:

(1) increases chemotaxis of neutrophils to increase production of IL-8, which effectively causes living cells in themselves to offer better defensive functions;

(2) increases production of matrix metalloprotease (MMP), which catalyzes to split necrotic tissue proteins and cleans the wound;

(3) increases production of an epidermal growth factor (EGF), which effectively stimulates fibroblast growth and promotes epithelialization; and (4) increases production of FGF2, which reduces PDLIM2 production, thereby significantly promotes fibroblast growth, and promotes angiogenesis, where PDLIM2 efficaciously eliminates or reduces the contraction of a wound site. The inventors also have found that the compound exhibits the effects (1) to (4) in combination, terminates inflammation at an early stage, promotes wound repair, and shortens the time necessary for healing. The present invention has been made on the basis of these findings.

Specifically, an aspect of the present invention provides a wound repair promoter including at least one active ingredient selected from the group consisting of compounds represented by Formula (1), salts of the compounds, and hydrates of the compounds or the salts, where Formula (1) is expressed as follows:

[Chem. 1]

(1)

wherein $R^1$ and $R^2$ are each, identically or differently, selected from hydrogen and a hydrocarbon group optionally having one or more substituents selected from the group consisting of halogens, $-COOR^3$, $-CONR^3_2$, $-COR^3$, $-CN$, $-NO_2$, $-NHCOR^3$, $-OR^3$, $-SR^3$, $-OCOR^3$, $-SO_3R^3$, and $-SO_2NR^3_2$, where $R^3$ is, identically or differently in each occurrence, selected from hydrogen and an optionally substituted aliphatic hydrocarbon group; and n represents an integer of 1 or more.

The wound repair promoter may be a mucosal wound repair promoter.

The wound repair promoter may also be a wound repair promoter for a tissue including a fibroblast.

The wound repair promoter may be a pharmaceutical preparation for preventing or treating a periodontal disease.

The wound repair promoter may be a substance selected from the group consisting of dentifrices, mouthwashes, mouth sprays, gargles, chewable tablets, troches or drops, tablets, candies, chewing gum, ointments, plasters or adhesive skin patches, nasal drops, and eye drops, where the substance includes at least one active ingredient selected from the group consisting of compounds represented by Formula (1), salts of the compounds, and hydrates of the compounds or the salts. Formula (1) is expressed as follows:

[Chem. 2]

(1)

wherein $R^1$ and $R^2$ are each, identically or differently, selected from hydrogen and a hydrocarbon group optionally having one or more substituents selected from the group consisting of halogens, $-COOR^3$, $-CONR^3_2$, $-COR^3$, $-CN$, $-NO_2$, $-NHCOR^3$, $-OR^3$, $-SR^3$, $-OCOR^3$, $-SO_3R^3$, and $-SO_2NR^3_2$, where $R^3$ is, identically or differently in each occurrence, selected from hydrogen and an optionally substituted aliphatic hydrocarbon group; and n represents an integer of 1 or more.

Advantageous Effects of Invention

The compounds represented by Formula (1) have approximately no cytotoxicity and are satisfactorily safe. The compounds represented by (1), when each formulated into a pharmaceutical preparation and applied to a wound site, act concertedly with a cytokine (such as TGF-β or another anti-inflammatory cytokine), which is secreted from immunocompetent cells to control inflammatory response in the wound site. The compounds thus primarily increase production of IL-8, MMP, FGF, and EGF, reduce production of PDLIM2, and increase production of FGF2, which effectively significantly accelerates fibroblast growth and efficaciously accelerates angiogenesis. Thus, the compounds can effectively terminate inflammation at an early stage, promote wound repair, and shorten the time necessary for healing.

The pharmaceutical preparation, when applied to such a wound site, can efficaciously hasten wound healing, can enhance biological barrier functions when biological functions have been lowered due to aging or a disease, and can prevent or minimize various diseases caused by such biological barrier function reduction. The pharmaceutical preparation can offer such effects not only to humans, but also to other animals.

For example, the pharmaceutical preparation, when applied to the oral mucosa, can enhance barrier functions, can inhibit or reduce the onset of periodontal diseases, and can prevent or minimize periodontal tissue loss due to such periodontal diseases. The pharmaceutical preparation can also heal and recover a periodontal tissue which has been once lost. The pharmaceutical preparation is very efficacious typically as a pharmaceutical preparation for preventing and/or treating periodontal diseases.

DESCRIPTION OF EMBODIMENTS

As used herein, the term "wound" refers to such a state or condition that a tissue loses its surface by any cause such as abrasion, laceration, incised wound, contusion, ulcer, bedsore, diabetic ulcer, thermal injury, inflammation, or necrotic cell death. Examples of the tissue include skin and mucosa. The skin includes epidermis, dermis, and hypodermal tissues. The mucosa includes an epithelium (or, mucosal epithelium), proper mucous membrane, and submucosa.

Wound Repair Promoter

A wound repair promoter (wound healing promoter) according to an embodiment of the present invention includes at least one active ingredient selected from the group consisting of compounds represented by Formula (1), salts of the compounds, and hydrates of the compounds or the salts. Such a compound represented by Formula (1), which contains at least one asymmetric atom, has at least two optical isomers. The compound represented by Formula (1) in the wound repair promoter according to the present invention may be a racemate, i.e., a mixture of equal parts of such optical isomers (or enantiomers), or may be an optically active substance (or one of enantiomers) resulting from optical resolution of the mixture of equal parts of the optical isomers. The racemate may be optically resolved by a well-known, common technique such as a diastereomeric salt technique, or a resolution technique using a chiral column. Formula (1) is expressed as follows:

[Chem. 3]

(1)

wherein $R^1$ and $R^2$ are each, identically or differently, selected from hydrogen and a hydrocarbon group optionally having one or more substituents selected from the group consisting of halogens, —$COOR^3$, —$CONR^3_2$, —$COR^3$, —CN, —$NO_2$, —$NHCOR^3$, —$OR^3$, —$SR^3$, —$OCOR^3$, —$SO_3R^3$, and —$SO_2NR^3_2$, where $R^3$ is, identically or differently in each occurrence, selected from hydrogen and an optionally substituted aliphatic hydrocarbon group; and n represents an integer of 1 or more.

Examples of the hydrocarbon group as $R^1$ and $R^2$ include aliphatic hydrocarbon groups, alicyclic hydrocarbon groups, aromatic hydrocarbon groups, and groups each including two or more of these groups bonded to each other via a single bond.

Of the aliphatic hydrocarbon groups, preferred are $C_1$-$C_{20}$ (containing 1 to 20 carbon atoms) aliphatic hydrocarbon groups, which are exemplified typically by alkyls containing about 1 to about 20 carbon atoms, such as methyl, ethyl, propyl, isopropyl, butyl, isobutyl, s-butyl, t-butyl, pentyl, hexyl, decyl, and dodecyl, of which $C_1$-$C_{10}$ alkyls are preferred, and $C_1$-$C_3$ alkyls are particularly preferred; alkenyls containing about 2 to about 20 carbon atoms, such as vinyl, allyl, and 1-butenyl, of which $C_2$-$C_{10}$ alkenyls are preferred, and $C_2$ or $C_3$ alkenyls are particularly preferred; alkynyls containing about 2 to about 20 carbon atoms, such as ethynyl and propynyl, of which $C_2$-$C_{10}$ alkynyls are preferred, and $C_2$ or $C_3$ alkynyls are particularly preferred.

Of the alicyclic hydrocarbon groups, preferred are $C_3$-$C_{20}$ alicyclic hydrocarbon groups, which are exemplified typically by cycloalkyls containing about 3 to about 20 carbon atoms, such as cyclopropyl, cyclobutyl, cyclopentyl, cyclohexyl, and cyclooctyl, of which $C_3$-$C_{15}$ cycloalkyls are preferred, and $C_5$-$C_8$ cycloalkyls are particularly preferred; cycloalkenyls containing about 3 to about 20 carbon atoms, such as cyclopentenyl and cyclohexenyl, of which $C_3$-$C_{15}$ cycloalkenyls are preferred, and $C_5$-$C_8$ cycloalkenyls are particularly preferred; and bridged hydrocarbon groups such as perhydronaphth-1-yl, norbornyl, adamantyl, tricyclo[5.2.1.0$^{2,6}$]dec-8-yl, and tetracyclo[4.4.0.1$^{2,5}$.1$^{7,10}$]dodec-3-yl.

Of the aromatic hydrocarbon groups, preferred are $C_6$-$C_{14}$ aromatic hydrocarbon groups such as phenyl and naphthyl, of which $C_6$-$C_{10}$ aromatic hydrocarbon groups are particularly preferred.

Non-limiting examples of the groups each including an aliphatic hydrocarbon group and an alicyclic hydrocarbon group bonded to each other include cycloalkyl-substituted alkyls such as cyclopentylmethyl, cyclohexylmethyl, and 2-cyclohexylethyl, of which $C_3$-$C_{20}$ cycloalkyl-substituted $C_1$-$C_4$ alkyls are typified. Non-limiting examples of the groups each including an aliphatic hydrocarbon group and an aromatic hydrocarbon group bonded to each other include aralkyls such as $C_7$-$C_{18}$ aralkyls; alkyl-substituted aryls such as phenyl or naphthyl substituted with one to about four $C_1$-$C_4$ alkyls.

The aliphatic hydrocarbon group as $R^3$ is exemplified as with the aliphatic hydrocarbon groups as $R^1$ and $R^2$.

Examples of the substituents which the aliphatic hydrocarbon group as $R^3$ may have include, but are not limited to, halogens, oxo, hydroxy, substituted oxys (such as $C_1$-$C_4$ alkoxys, $C_6$-$C_{10}$ aryloxys, $C_7$-$C_{16}$ aralkyloxys, and $C_1$-$C_4$ acyloxys), carboxy, substituted oxycarbonyls (such as $C_1$-$C_4$ alkoxycarbonyls, $C_6$-$C_{10}$ aryloxycarbonyls, and $C_7$-$C_{16}$ aralkyloxycarbonyls), substituted or unsubstituted carbamoyls (exemplified by carbamoyl, $C_1$-$C_4$ alkyl-substituted carbamoyls such as methylcarbamoyl, and $C_6$-$C_{10}$ aryl-substituted carbamoyls such as phenylcarbamoyl), cyano, nitro, substituted or unsubstituted aminos (exemplified by mono- or di-($C_1$-$C_4$ alkyl)aminos such as methylamino, dimethylamino, ethylamino, and diethylamino; 5- to 8-membered cyclic aminos such as 1-pyrrolidinyl, piperidino, and morpholino; $C_1$-$C_{10}$ acylaminos such as acetylamino, propionylamino, and benzoylamino; and sulfonylaminos such as benzenesulfonylamino and p-toluenesulfonylamino), sulfo, and heterocyclic groups. The hydroxy and the carboxy may each be protected with a protecting group common in the organic synthesis field.

The number n represents an integer of 1 or more and is typically an integer of 1 to 10.

Such compounds represented by Formula (1) are classified into categories [I] and [II] as follows:

[I] compounds of Formula (1) in which both the $OR^1$ group and the $OR^2$ group are OH groups (compounds (I)); and

[II] compounds of Formula (1) in which at least one of the $OR^1$ group and the $OR^2$ group is a group other than OH group (compounds (II)).

In the compounds (I), n is preferably an integer of 2 to 10, and particularly preferably an integer of 2 to 8.

In the compounds (II), n is preferably an integer of 1 to 8, and particularly preferably an integer of 2 to 6.

In the compounds (II), the $OR^1$ group and the $OR^2$ group are in a combination preferably selected from combinations [II-i] to [II-v] below. In particular, when n in Formula (1) is 1 or 2, the two groups are in a combination preferably selected from the combinations [II-i] to [II-iv]; and when n in Formula (1) is an integer of 3 or more, the two groups are preferably in the combination [II-v].

[II-i] Combination of a group represented by Formula (i-1) and a group represented by Formula (i-2):

[Chem. 4]

(i-1)

(i-2)

wherein $R^4$ represents an optionally substituted aromatic hydrocarbon group or an optionally substituted heterocyclic group, and wherein $R^5$, $R^6$, and $R^7$ each represent, identically or differently, a group selected from the class consisting of hydrogen, an optionally substituted aliphatic hydrocarbon group, an optionally substituted aromatic hydrocarbon group, halogens, —$COOR^8$, —$CONR^8_2$, —$COR^8$, —$OCOR^8$, —$CF_3$, —CN, —$SR^8$, —$SOR^8$, —$SO_2R^8$, —$SO_2NR^8_2$, —$PO(OR^8)_2$, and —$NO_2$, where $R^8$ is selected from hydrogen, alkyl, and alkenyl, and where two groups selected from $R^5$ to $R^7$ may combine with each other to form a ring with the carbon atom or atoms to which the two groups are bonded in the group represented by Formula (i-2).

The aliphatic hydrocarbon group and the aromatic hydrocarbon group are exemplified as with the aliphatic hydrocarbon groups and the aromatic hydrocarbon groups as $R^1$ and $R^2$.

The "heterocycle" constituting the heterocyclic group includes aromatic heterocycles and non-aromatic heterocycles. Such heterocycles are exemplified typically by 3- to 10-membered rings containing at least one heteroatom (such as oxygen, sulfur, or nitrogen) as an atom constituting the ring, of which 4- to 6-membered rings are preferred; and fused rings each including two or more of these rings fused with each other. Specifically, such heterocycles are exemplified typically by heterocycles containing oxygen as a heteroatom; heterocycles containing sulfur as a heteroatom; and heterocycles containing nitrogen as a heteroatom. Non-limiting examples of the oxygen-containing heterocycles include 3-membered rings such as oxirane ring; 4-membered rings such as oxetane ring; 5-membered rings such as furan, tetrahydrofuran, oxazole, isoxazole, and γ-butyrolactone rings; 6-membered rings such as 4-oxo-4H-pyran, tetrahydropyran, and morpholine rings; fused rings such as benzofuran, isobenzofuran, 4-oxo-4H-chromene, chroman, and isochroman rings; and bridged rings such as 3-oxatricyclo[4.3.1.1$^{4,8}$]undecan-2-one and 3-oxatricyclo[4.2.1.0$^{4,8}$]nonan-2-one rings. Non-limiting examples of the sulfur-containing heterocycles include 5-membered rings such as thiophene, triazole, isothiazole, and thiadiazole rings; 6-membered rings such as 4-oxo-4H-thiopyran ring; and fused rings such as benzothiophene ring. Non-limiting examples of the nitrogen-containing heterocycles include 5-membered rings such as pyrrole, pyrrolidine, pyrazole, imidazole, and triazole rings; 6-membered rings such as isocyanurate, pyridine, pyridazine, pyrimidine, pyrazine, piperidine, and piperazine rings; and fused rings such as indole, indoline, quinoline, acridine, naphthyridine, quinazoline, and purine rings. The heterocyclic group is a group corresponding to any of the heterocycles, except for removing one hydrogen atom from the structural formula of the heterocycle.

The substituents which the aliphatic hydrocarbon group, the aromatic hydrocarbon group, and the heterocyclic group as $R^4$ to $R^7$ may have are exemplified as with the substituents which the aliphatic hydrocarbon groups as $R^3$ may have.

[II-ii] Combination of a group represented by Formula (ii-1) and a group represented by Formula (ii-2):

[Chem. 5]

(ii-1)

(ii-2)

wherein $R^9$ is selected from hydrogen, optionally substituted alkyl, and optionally substituted aryl; and $R^{10}$ is selected from hydrogen and a group represented by Formula (r10):

[Chem. 6]

(r10)

wherein $R^{11}$ is selected from hydrogen, methyl, and ethyl; n1 represents an integer of 0 to 4, n2 represents 0 or 1, and n3 represents an integer of 0 to 4, where two or three of n1, n2, and n3 may be identical; $X^1$ is selected from an amide bond and alkenylene; $X^2$ represents a group selected from the class consisting of —COOR$^3$, —CONR$^3{}_2$, —COR$^3$, —CN, —NO$_2$, —NHCOR$^3$, —OR$^3$, —SR$^3$, —OCOR$^3$, —SO$_3$R$^3$, and —SO$_2$NR$^3{}_2$, where R$^3$ is as defined above, and wherein Y$^1$ represents a group selected from the class consisting of hydrogen, alkyl, alkenyl, alkoxy, alkenyloxy, halogens, —COOR$^8$, —CONR$^8{}_2$, —COR$^8$, —OCOR$^8$, —CF$_3$, —CN, —SR$^8$, —SOR$^8$, —SO$_2$R$^8$, —SO$_2$NR$^8{}_2$, —PO(OR$^8$)$_2$, and —NO$_2$, where R$^8$ is as defined above; and Y$^2$ represents a group selected from the class consisting of hydrogen, optionally substituted alkyl, optionally substituted alkenyl, —COOR$^3$, —CONR$^3{}_2$, —COR$^3$, —CN, —NO$_2$, —NHCOR$^3$, —OR$^3$, —SR$^3$, —OCOR$^3$, —SO$_3$R$^3$, and —SO$_2$NR$^3{}_2$, where R$^3$ is as defined above, and where Y$^1$ and Y$^2$ may combine with each other to form a ring with the carbon atoms constituting the benzene ring in Formula (ii-2).

[II-iii] Combination of optionally substituted alkoxy and a group selected from groups represented by Formulae (iii-1) to (iii-4):

[Chem. 7]

wherein R$^{12}$ is selected from hydrogen, methyl, and ethyl; and Y$^1$ and Y$^2$ are as defined above, where Y$^1$ and Y$^2$ may combine with each other to form a ring with the carbon atoms constituting the specified aromatic ring.

[II-iv] Combination in which the OR$^1$ group and the OR$^2$ group are each, identically or differently, selected from groups represented by Formula (iv-1):

[Chem. 8]

wherein Y$^1$ and Y$^2$ are as defined above, where Y$^1$ and Y$^2$ may combine with each other to form a ring with the carbon atoms constituting the specified benzene ring.

[II-v] Combination of hydroxy and optionally substituted aliphatic hydrocarbon-oxy (preferably C$_1$-C$_6$ alkoxy).

The substituents which the alkyl, alkenyl, aryl, alkoxy, and aliphatic hydrocarbon-oxy may have are exemplified as with the substituents which the aliphatic hydrocarbon group as R$^3$ may have.

The aliphatic hydrocarbon moiety constituting the aliphatic hydrocarbon-oxy is exemplified as with the aliphatic hydrocarbon groups as R$^1$ and R$^2$.

Of the compounds (I), preferred are compounds (including optical isomers) represented by Formulae (I-1) to (I-5):

[Chem. 9]

Of the compounds (II), preferred are compounds (including optical isomers) represented by Formulae (II-1) and (II-2):

[Chem. 10]

The compounds represented by Formula (1) may be hydrates, or the compounds represented by Formula (1) or hydrates of the compounds may form salts. Non-limiting examples of the salts of the compounds represented by Formula (1) or of the hydrates of the compounds include alkali metal salts such as sodium salts and potassium salts;

alkaline earth metal salts such as magnesium salts, calcium salts, and barium salts; ammonium salts (salts with ammonia); salts with a nitrogen-containing organic base such as trimethylamine, triethylamine, tributylamine, pyridine, quinoline, piperidine, imidazole, picoline, dimethylaminopyridine, N,N-dimethylaniline, N-methylpiperidine, N-methylmorpholine, diethylamine, cyclohexylamine, procaine, dibenzylamine, N-benzyl-β-phenethylamine, 1-ephenamine, N,N'-dibenzylethylenediamine, or N-methyl-D-glucamine; salts with a basic amino acid such as lysine, arginine, or ornithine; transition metal salts; salts with an inorganic acid such as hydrochloric acid, sulfuric acid, nitric acid, phosphoric acid, or boric acid; and salts with an organic acid such as oxalic acid, acetic acid, or p-toluenesulfonic acid.

Of the compounds represented by Formula (1), the compounds (I) can be produced typically through Steps [1] to [4]; and the compounds (II) can be produced typically through Steps [1] to [10] as described later.

In the formulae below, n is as defined above; X represents a halogen (fluorine, chlorine, bromine, or iodine); R and R' each represent, identically or differently in each occurrence, $C_1$-$C_{10}$ alkyl; R" represents an amino-protecting group; and DPR represents a deprotectant for the protected amino. Non-limiting examples of the amino-protecting group include $C_1$-$C_{10}$ alkyls, $C_7$-$C_{18}$ aralkyls, acyls ($R^a$C(=O) groups where $R^a$ is $C_1$-$C_{10}$ alkyl), alkoxycarbonyls ($R^B$OC(=O) groups where $R^b$ is $C_1$-$C_{10}$ alkyl), optionally substituted benzyloxycarbonyl, optionally substituted phenylmethylidene, and optionally substituted diphenylmethylidene. Non-limiting examples of such substituents include halogens, $C_1$-$C_3$ alkoxys, and nitro.

[Chem. 11]

[Chem. 12]

ハロゲン化剤 : Halogenating agent

[Chem. 13]

The reaction of Step [1] is a Michaelis-Arbuzov reaction, which reacts a dihalogenated alkylene represented by Formula (2) with a phosphorous ester represented by Formula (3) to give a phosphonoalkanoic acid represented by Formula (4). The phosphorous ester represented by Formula (3) is used in an amount of typically about 0.1 to about 1.0 mole per mole of the dihalogenated alkylene represented by Formula (2).

The reaction of Step [1] is performed at a temperature of preferably, for example, about 130° C. to about 140° C. for a time of typically about 0.5 to about 2 hours.

The reaction of Step [2] reacts the phosphonoalkanoic acid represented by Formula (4), which is obtained through the reaction of Step [1], with a compound represented by Formula (5) to give a compound represented by Formula (6). The compound represented by Formula (5) is used in an amount of typically about 0.7 to about 1.3 moles per mole of the phosphonoalkanoic acid represented by Formula (4).

The reaction of Step [2] is preferably performed in the presence of a base, to efficaciously promote the progress of the reaction. Non-limiting examples of the base include carbonates such as potassium hydrogencarbonate, sodium hydrogencarbonate, potassium carbonate, and sodium carbonate, of which alkali metal carbonates are typified; alkali metal hydroxides such as sodium hydroxide and potassium hydroxide; alkaline earth metal hydroxides such as calcium hydroxide and magnesium hydroxide; phosphates such as sodium dihydrogenphosphate and potassium dihydrogenphosphate, of which alkali metal phosphates are typified; carboxylates such as sodium acetate and potassium acetate, of which alkali metal carboxylates are typified; organic bases such as triethylamine and pyridine; metal alkoxides such as sodium methoxide and sodium ethoxide, of which alkali metal alkoxys are typified; and metal hydrides such as sodium hydride. Each of different bases may be used alone or in combination. The base is used in an amount of typically about 0.9 to about 1.1 moles per mole of the phosphonoalkanoic acid represented by Formula (4).

The reaction of Step [2] is preferably performed in the presence of a solvent. Examples of the solvent include, but are not limited to, ketones such as acetone and ethyl methyl ketone; ethers such as tetrahydrofuran and dioxane; nitriles such as acetonitrile; sulfoxides such as dimethyl sulfoxide; sulfones such as sulfolane; esters such as ethyl acetate; amides such as dimethylformamide; alcohols such as methanol, ethanol, and t-butyl alcohol; hydrocarbons such as pentane, hexane, and petroleum ether; aromatic hydrocarbons such as benzene, toluene, and xylene; halogen-containing compounds such as methylene chloride, chloroform, bromoform, chlorobenzene, and bromobenzene; chain carbonates such as dimethyl carbonate, diethyl carbonate, and ethyl methyl carbonate; and cyclic carbonates such as ethylene carbonate and propylene carbonate. Each of different solvents may be used alone or in combination.

The reaction of Step [2] is performed at a temperature of preferably, for example, about 100° C. to about 110° C. for a time of typically about 6 to about 24 hours.

The reaction of Step [3] deprotects the protected carboxy group (—COOR'), the protected amino group (—NHR"), and the protected phosphonate group (—P(=O)(OR)$_2$) in the compound represented by Formula (6), which is obtained through the reaction of Step [2], to give a compound represented by Formula (7). The protected groups can be deprotected by reacting the compound with a deprotectant. The deprotectant (represented by "DPR" in the formulae) for use herein is advantageously selected from strong bases (such as sodium hydroxide) or strong acids (such as hydrochloric acid).

The reaction of Step [3] is performed at a temperature of preferably, for example, about 90° C. to about 100° C. for a time of typically about 20 to about 24 hours.

The reaction of Step [4] reacts the compound represented by Formula (7), which is obtained through the reaction of Step [3], with a compound capable of trapping the deprotectant, to trap the deprotectant to thereby give a compound (I). When the deprotectant is, for example, hydrochloric acid, the compound capable of trapping the deprotectant for use herein is preferably propylene oxide. The compound capable of trapping the deprotectant is used in an amount of typically about 3.0 to about 6.0 moles per mole of the compound represented by Formula (7).

Step [5] introduces a protecting group into the carboxy group of the compound (I). The protecting group can be introduced typically by reacting the compound (I) with $R^COH$, where $R^C$ represents optionally substituted aryl or aralkyl and is preferably benzyl or 4-nitrobenzyl. This reaction is preferably performed in the presence of an acid catalyst (such as hydrochloric acid) at an ambient temperature around room temperature, and is performed for a time of typically about 12 to about 24 hours.

Step [6] introduces a protecting group into the amino group of the compound (I). The protecting group can be introduced typically by adding R"X dropwise to the compound (I) dissolved in a solvent to react R"X with the compound (I). This reaction is preferably performed in the presence of a base (such as sodium hydrogencarbonate).

Non-limiting examples of the solvent usable herein include water, halogenated hydrocarbon solvents, saturated or unsaturated hydrocarbon solvents, aromatic hydrocarbon solvents, and ether solvents. Each of different solvents may be used alone or in combination.

The dropwise addition is preferably performed at a temperature equal to or lower than room temperature and particularly preferably performed at around 0° C. The reaction is performed for a time of typically about 0.5 to about 2 hours. After the completion of dropwise addition, the reaction mixture is preferably aged with stirring at a constant temperature of typically 25° C. to 30° C. for a time of typically about 10 to about 24 hours.

Step [7] substitutes or replaces two hydroxy groups in the phosphate group with halogen atoms. This step can be performed typically by reacting the compound obtained through Steps [5] and [6] with a halogenating agent in the presence of a catalyst and a solvent. The catalyst usable herein may for example be N,N-dimethylformamide. The solvent usable herein may be one or more solvents selected typically from halogenated hydrocarbon solvents and ether solvents. Non-limiting examples of the halogenating agent include oxalyl hydrochloride, thionyl chloride, phosphorus pentachloride, and phosphorus oxychloride. Each of them may be used alone or in combination. The reaction is preferably performed at a temperature around room temperature for about one hour.

Step [8] reacts the compound obtained through Step [7] with $R^1OH$ to replace one of the halogen atoms bonded to the phosphorus atom with $OR^1$. This reaction is preferably performed in the presence of a base. Non-limiting examples of the base include triethylamine, tributylamine, diisopropylethylamine, N-methylpiperidine, N-methylmorpholine, diethylisopropylamine, N-methylimidazole, and pyridine. The reaction is preferably performed in the presence of a solvent, which is preferably dry dichloromethane. The reaction is preferably performed by stirring the materials at around −65° C. for about 30 minutes, gradually rising the temperature of the mixture up to room temperature, and then stirring the mixture while holding the temperature at room temperature, for about 1 to about 3 hours.

Step [9] reacts the compound (1'-4) with $R^2OH$ to replace the other halogen atom bonded to the phosphorus atom with $OR^2$. Step [9] can be performed by a procedure similar to that in Step [8], except for using $R^2OH$ instead of $R^1OH$.

Step [10] deprotects the protected carboxy and amino groups and can be performed by a technique such as a catalytic hydrogen reduction technique or a deprotection technique using aluminum chloride. The catalytic hydrogen reduction technique bubbles hydrogen gas into the compound obtained through Step [9], in the presence of a palladium catalyst or a platinum catalyst, where the palladium catalyst includes palladium supported on a support such as activated carbon or barium sulfate. The deprotection technique using aluminum chloride reacts the compound obtained through Step [9] with anisole in a solvent (such as dry nitromethane or another high polar solvent) further containing aluminum trichloride.

Each reaction in each step may be performed in any reaction-harmless atmosphere such as an air atmosphere, nitrogen atmosphere, or argon atmosphere. The reaction can be performed at normal atmospheric pressure, under reduced pressure, or under pressure (under a load). The reaction can be performed according to any system such as a batch system, semi-batch system, or continuous system.

After the completion of each step, the obtained reaction product may be purified typically by a separation means such as filtration, concentration, distillation, extraction, crystallization, adsorption, recrystallization, or column chromatography, or a separation means as any combination of them.

The hydrate of the compound represented by Formula (1) can be produced by subjecting the compound (I) or the compound (II), which is obtained by the process, to a crystallization treatment using water and a water-soluble solvent.

The water-soluble solvent is preferably selected from organic solvents that are soluble in or miscible with water in any proportions at room temperature (25° C.) and preferably selected from organic solvents having a water solubility of 50% or more, more preferably 80% or more, and particularly preferably 95% or more.

The water-soluble solvent for use herein is preferably selected from alcohols, such as methanol, ethanol, and other $C_1$-$C_5$ lower alcohols.

The salt of the compound represented by Formula (1) can be produced typically by reacting the compound (I) or the compound (II), which is obtained by the process, typically with a basic compound, ammonia, a nitrogen-containing organic base, a basic amino acid, an inorganic acid, or an organic acid. Non-limiting examples of the basic compound include sodium hydroxide, potassium hydroxide, magnesium hydroxide, calcium hydroxide, and barium hydroxide. Non-limiting examples of the nitrogen-containing organic base include trimethylamine, triethylamine, tributylamine, pyridine, quinoline, piperidine, imidazole, picoline, dimethylaminopyridine, N,N-dimethylaniline, N-methylpiperidine, N-methylmorpholine, diethylamine, cyclohexylamine, procaine, dibenzylamine, N-benzyl-β-phenethylamine, 1-ephenamine, N,N'-dibenzylethylenediamine, and N-methyl-D-glucamine. Examples of the basic amino acid include, but are not limited to, lysine, arginine, and ornithine. Non-limiting examples of the inorganic acid include hydrochloric acid, sulfuric acid, nitric acid, phosphoric acid, and boric acid. Non-limiting examples of the organic acid include oxalic acid, acetic acid, and p-toluenesulfonic acid.

The wound repair promoter according to the present invention includes at least one active ingredient (including an optical isomer) selected from the group consisting of the compounds represented by Formula (1) (for example, at least one of the compound (I) and the compound (II)), salts of the compounds, and hydrates of the compounds or the salts, and preferably includes at least one active ingredient selected from the group consisting of the compounds represented by Formulae (I-1) to (I-5) and Formulae (II-1) and (II-2), salts of the compounds, and hydrates of the compounds or the salts.

In the wound repair promoter according to the present invention, the content of the compound represented by Formula (1), a salt of the compound, or a hydrate of the compound or the salt can be adjusted appropriately according to the intended use, where, when two or more different active ingredients are present, the term "content" is read as "total content of them". For example, when the wound repair promoter according to the present invention is used for preventing or treating periodontal diseases, the content is typically 0.001 to 500 μg/mL, preferably 0.005 to 300 μg/mL, more preferably 0.01 to 200 μg/mL, still more preferably 0.01 to 100 μg/mL, particularly preferably 0.01 to 10 μg/mL, especially preferably 0.01 to 1.0 μg/mL, and most preferably 0.01 to 0.5 μg/mL.

In addition to at least one of the compounds represented by Formula (1), salts of the compounds, and hydrates of the compounds or the salts, the wound repair promoter according to the present invention may further contain one or more other components. Such other components may be appropriately selected according to the intended use. For example, when the wound repair promoter according to the present invention is used for preventing or treating periodontal diseases, examples of the other components include components commonly contained typically in dentifrices, mouthwashes, oral sprays, oral liniments (such as oral gels and oral ointments), throat sprays, gargles, dermatological pastes, soft pastes, throat liniments, chewable tablets, troches or drops, and other substances.

The wound repair promoter according to the present invention, when applied to a wound site, promotes TGF-β production, as compared with the case without application of the wound repair promoter according to the present invention, where TGF-β is one of anti-inflammatory cytokines. The wound repair promoter according to the present invention, when applied to a normal epithelium, causes approximately no increase in TGF-β production. Thus, the wound repair promoter according to the present invention has approximately no cytotoxicity and is satisfactorily safe.

The wound repair promoter according to the present invention, when applied to a wound site (such as fibroblasts which undergo an inflammatory response due typically to LPS stimulation), promotes IL-8 production at an early stage, but then tends to reduce IL-8 production, as compared with the case without application of the wound repair promoter according to the present invention. The early stage is typically 0.5 to 60 hours, preferably 1 to 48 hours, and particularly preferably 2 to 36 hours, after the application. The IL-8 production also serves as an index of the degree of inflammation, and reduction in IL-8 production indicates that the inflammation is relieved in its degree. This demonstrates that the wound repair promoter according to the present invention efficaciously accelerates IL-8 production, thereby increases chemotaxis of neutrophils, causes inflammation to terminate at an early stage, and accelerates wound healing.

The wound repair promoter according to the present invention, when applied to a normal epithelium (or fibroblasts without inflammatory response), causes approximately no increase in IL-8 production. Thus, the wound repair promoter according to the present invention has approximately no cytotoxicity and is satisfactorily safe.

The wound repair promoter according to the present invention, when applied to a wound site, promotes production of an MMP as compared with the case without application of the wound repair promoter according to the present invention, where MMP catalyzes to split necrotic tissue proteins and cleans the wound. The MMP herein is, for example, at least one MMP selected from MMP3, MMP9, and MMP13. The wound repair promoter according to the present invention, when applied to a normal epithelium (or fibroblasts without TGF-β addition), causes approximately no increase in MMP production.

The wound repair promoter according to the present invention, when applied to a wound site, promotes production of an FGF (specifically, FGF2) as compared with the case without application of the wound repair promoter according to the present invention, where the FGF efficaciously promotes growth of fibroblasts and endothelial cells and promotes formation of a granulation tissue. The wound repair promoter according to the present invention, when applied to a tissue or cell in the absence of TGF-β, causes approximately no increase in FGF production. TGF-β is present in a physiological condition of a wound site in the living body, and the presence of TGF-β allows the wound repair promoter according to the present invention, when applied to such a wound site, to promote FGF production.

The wound repair promoter according to the present invention, when applied to a wound site, promotes an EGF (such as amphiregulin) production, as compared with the case without application of the wound repair promoter according to the present invention, where the EGF efficaciously stimulates fibroblast growth and promotes epithelialization. The wound repair promoter according to the present invention, when applied to a normal epithelium, causes approximately no increase in EGF production.

The wound repair promoter according to the present invention, when applied to a wound site, reduces PDLIM2 production as compared with the case without application of the wound repair promoter according to the present invention. The reduction in PDLIM2 production induces FGF production, to stimulate fibroblast growth.

The wound repair promoter according to the present invention, when applied to a wound site, promotes production of a hyaluronic acid (for example, through at least one selected from HAS1, HAS2, and HAS3), as compared with the case without application of the wound repair promoter according to the present invention. The wound repair promoter according to the present invention, when applied to a normal epithelium, causes approximately no increase in hyaluronic acid production.

The wound repair promoter according to the present invention, when applied to a wound site, allows the compound represented by Formula (1) to coordinate with a cytokine (such as TGF-β or another anti-inflammatory cytokine) secreted from immunocompetent cells, to control the inflammatory response of the wound site. Thus, the wound repair promoter primarily increases production of IL-8, MMP, FGF, EGF, and hyaluronic acid and reduces production of PDLIM2. This allows the wound repair promoter to effectively terminate inflammation at an early stage, to promote wound repair, and to shorten the time necessary for healing.

The wound repair promoter according to the present invention may be used as a pharmaceutical preparation in the form typically of a paste, gel, liquid, milky lotion, or cream. The wound repair promoter may also be used as an aerosol pharmaceutical preparation or a sprayable pharmaceutical preparation.

The wound repair promoter according to the present invention is useful as a repair promoter for a wound such as abrasion, laceration, incised wound, contusion, ulcer, burn injury, bedsore, diabetic ulcer, thermal injury, inflammation, or necrotic cell death. The wound repair promoter is advantageously usable as a repair promoter for a wound in the skin or mucosa, exemplified by ocular mucosa (such as cornea, corneal epithelium, or conjunctiva), nasal mucosa, oral mucosa, gastric mucosa, intestinal mucosa, endometrium, or olfactory epithelium.

The wound repair promoter according to the present invention is also advantageously usable as a wound repair promoter in a tissue including a fibroblast (fibroblast-containing tissue).

The wound repair promoter according to the present invention is advantageously usable for wound repair in the skin (epidermis, dermis, and hypodermal tissues). The wound repair promoter, when the wound is such a severe one as to cause deficiency not only in the epidermis, but also in a portion of the dermis, is efficacious for wound repair promotion. Specifically, the wound repair promoter according to the present invention is also advantageously usable as a wound repair promoter for the dermis.

The wound repair promoter according to the present invention, when applied to a skin wound (preferably a dermal wound), is preparable and usable typically as any of liniments (such as ointments, creams, lotions, and gels), plasters or adhesive skin patches (such as adhesive plasters and tapes), nasal drops, and eye drops. These can be prepared by a common procedure.

The wound repair promoter according to the present invention, particularly when applied to the oral mucosa (for example, when used for preventing or treating periodontal diseases), is preparable and usable typically as any of dentifrices such as toothpaste, liquid dentifrices, liquid viscous dentifrices, and tooth wet powder; mouthwashes; mouth sprays; oral liniments such as oral gels and oral ointments; throat sprays; gargles; dermatological pastes; soft pastes; throat liniments; chewable tablets; troches or drops; tablets; candies; and chewing gum. These can be prepared by a common procedure.

EXAMPLES

The present invention will be illustrated in further detail with reference to several examples below. It should be noted, however, that the examples are by no means intended to limit the scope of the invention.

Preparation Example 1

Preparation of D-2-amino-6-phosphonohexanoic acid monohydrate

Triethyl phosphite (5 ml, 29 mmol) was combined with 1,4-dibromobutane (25 g, 116 mmol), the mixture was raised in temperature up to 140° C. with stirring on an oil bath, heated at the same temperature for 30 minutes, and then naturally cooled. When the mixture was cooled down to around 40° C., the pressure was reduced down to about 1 mmHg, and the mixture was heated up to around 120° C. to distill off excess dibromobutane. This gave, as the residue, colorless, odorless, oily diethyl 4-bromobutylphosphonate (7.4 g, yield: 93%).

Diethyl 4-bromobutylphosphonate (7.4 g, 27 mmol) was combined with toluene (20 mL), diethyl carbonate (10 mL), diethyl acetamidomalonate (4.4 g, 20 mmol), and 60% sodium hydride (1.1 g, 26 mmol) washed with hexane, and the mixture was refluxed at 110° C. After being refluxed for 24 hours, the mixture was cooled down to room temperature, filtered through Celite to remove solids, and the filtrate was concentrated in a vacuum. This gave brown, oily diethyl 2-acetamido-2-[4-(diethoxyphosphoryl)butyl]malonate (10.1 g, in quantitative yield).

Diethyl 2-acetamido-2-[4-(diethoxyphosphoryl)butyl]malonate (10.1 g) was dissolved in 6 N hydrochloric acid (50 mL), followed by refluxing for 24 hour. Subsequent vacuum concentration gave brown, oily DL-2-amino-6-phosphonohexanoic acid hydrochloride (3.3 g, yield: 65%).

DL-2-Amino-6-phosphonohexanoic acid hydrochloride (3.3 g, 13 mmol) was dissolved in water (3.5 mL). The solution with vigorous stirring and cooling at 5° C. to 10° C. was combined with propylene oxide (3.5 mL, 50 mmol) added dropwise, and simultaneously, combined with ethanol (18 mL) added dropwise, followed by stirring at room temperature for 3 days. The precipitated crystals were collected by filtration, washed with ethanol, and dried at 40° C. under vacuum. This gave colorless, powdery DL-2-amino-6-phosphonohexanoic acid monohydrate (1.6 g, yield: 55%).

DL-2-Amino-6-phosphonohexanoic acid monohydrate (1.6 g) and L-p-hydroxyphenylglycine (HPGM, 1.4 g) were dissolved in water (18 mL) with heating, the solution was combined with methanol (30 mL) added gradually at 70° C., the mixture was then slowly cooled, and stirred at 25° C. for 3 hours. The precipitated crystals were collected by filtration, washed, and dried. This gave colorless crude crystals of D-2-amino-6-phosphonohexanoic acid L-HPGM salt monohydrate (1 g).

The crude crystals of D-2-amino-6-phosphonohexanoic acid L-HPGM salt monohydrate (1 g) were combined with water (6 mL), heated to 75° C. with stirring, and combined with methanol (26 mL) added dropwise. The mixture was slowly cooled, and stirred at 15° C. for 3 hours. The precipitated crystals were collected by filtration, washed, and dried. This gave recrystallized crystals of D-2-amino-6-phosphonohexanoic acid L-HPGM salt monohydrate (0.8 g).

The recrystallized crystals of D-2-amino-6-phosphonohexanoic acid L-HPGM salt monohydrate (0.8 g) were dissolved in pure water, and the solution was slowly passed through an ion exchange resin AMBERLITE IR-120 (H$^+$) (trade name, supplied by ORGANO CORPORATION) (5 mL). After the resin was thoroughly washed with pure water, the passed liquid and the washings were combined and concentrated. The residual solids were combined with and dispersed in methanol (5 mL), collected by filtration, washed with methanol, and dried. This gave colorless crystals of D-2-amino-6-phosphonohexanoic acid monohydrate (hereinafter also referred to as "D-AP6") (0.4 g), which is represented by Formula (I-3'):

[Chem. 14]

(I-3')

wherein the asterisk marks an asymmetric atom.

Examples 1 to 5

A compound represented by Formula (II-2) (trade name GGsTop, supplied by Wako Pure Chemical Industries, Ltd., hereinafter also referred to as "Nahlsgen") was diluted with water and yielded a pharmaceutical preparation (1) (concentration: 0.01 µg/mL), a pharmaceutical preparation (2) (concentration: 0.1 µg/mL), a pharmaceutical preparation (3) (concentration: 1.0 µg/mL), a pharmaceutical preparation (4) (concentration: 10.0 µg/mL), and a pharmaceutical preparation (5) (concentration: 100 µg/mL). Formula (II-2) is expressed as follows:

[Chem. 15]

(II-2)

Evaluation for Safety

The pharmaceutical preparations obtained in Examples 1 to 5 were each applied to gingival fibroblasts (clinical sample (healthy gingiva); passage number: 7 to 10 passages) and were evaluated for toxicity (or harmfulness) by measurement of IL-8 production. A specimen using water instead of the pharmaceutical preparations obtained in Examples 1 to 5 was used as a control.

Figure 1:
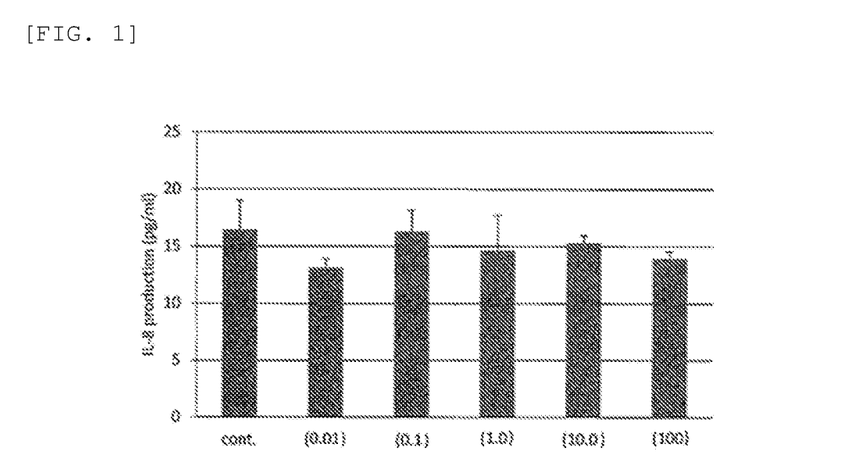
FIG. 1 is a graph illustrating safety evaluation results of pharmaceutical preparations obtained in working examples.

The results demonstrate that none of the pharmaceutical preparations obtained in the examples had an IL-8 production exceeding that of the control. This indicates that the pharmaceutical preparations have approximately no toxicity (see FIG. 1).

Evaluation for Healing Promotion Effect

A mixture (1) or a mixture (2) was applied to gingival fibroblasts (clinical sample (healthy gingiva); passage number: 7 to 10 passages), and the IL-8 production after 24 hours was measured. The mixture (1) is a mixture of the pharmaceutical preparation obtained in Example 1 and *Porphyromonas gingivalis* (*P. gingivalis*)-derived LPS (concentration: 1.0 μg/mL) (indicated as "LPS+(0.01)" in the figure). The mixture (2) is a mixture of the pharmaceutical preparation obtained in Example 2 and *P. gingivalis*-derived LPS (concentration: 1.0 μg/mL) (indicated as "LPS+(0.1)" in the figure). Instead of each of the mixtures of the pharmaceutical preparations obtained in the examples and *P. gingivalis*-derived LPS, the application of *P. gingivalis*-derived LPS (concentration: 1.0 μg/mL) alone gave a comparative example (hereinafter also referred to as "LPS alone"; indicated as "LPS" in the figure). The application of water alone gave a control.

Figure 2:
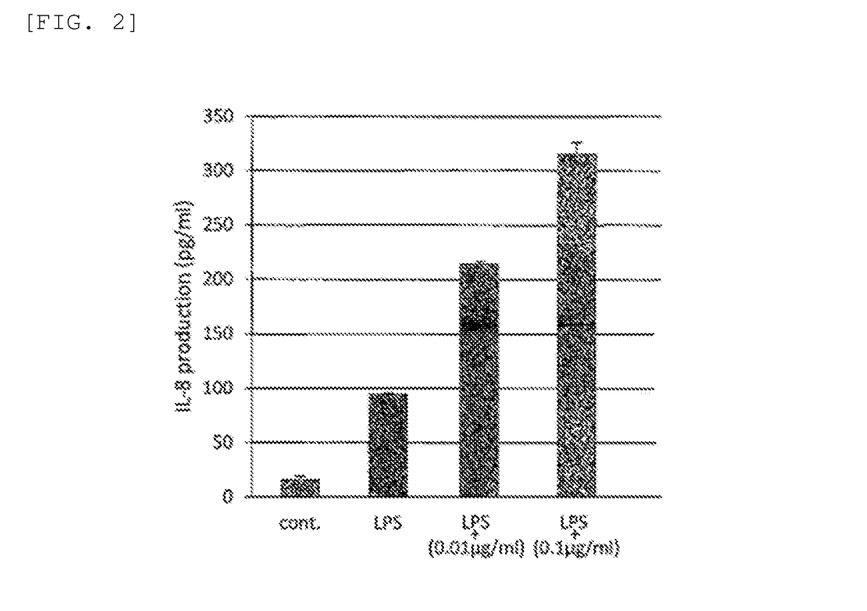
FIG. 2 is a graph illustrating initial IL-8 production promoting effects of the pharmaceutical preparations obtained in the examples.

The results demonstrate that the mixture (1) or the mixture (2), when applied, increases the IL-8 production as compared with the application of LPS alone (see FIG. 2). The increased IL-8 production in turn increases chemotaxis of neutrophils, which are immunocompetent cells, and leads to acceleration of healing. This indicates that the mixture (1) and the mixture (2) are efficacious for healing promotion.

Time-Dependent Change of IL-8 Production

The mixture (2) was applied to gingival fibroblasts (clinical sample (healthy gingiva); passage number: 7 to 10 passages), and the IL-8 production was measured 4 hours, 24 hours, and 72 hours after the application, where the mixture (2) is a mixture of the pharmaceutical preparation obtained in Example 2 and *P. gingivalis*-derived LPS (concentration: 1.0 μg/mL). Instead of the mixture (2), the application of LPS alone gave a comparative example; the application of the pharmaceutical preparation obtained in Example 2 alone gave a referential example (in FIG. 3, indicated as "(0.1)"); and the application of water alone gave a control. The IL-8 production (IL-8 yield) was determined by measuring the supernatant protein content by enzyme-linked immunosorbent assay (ELISA) technique.

Figure 3:
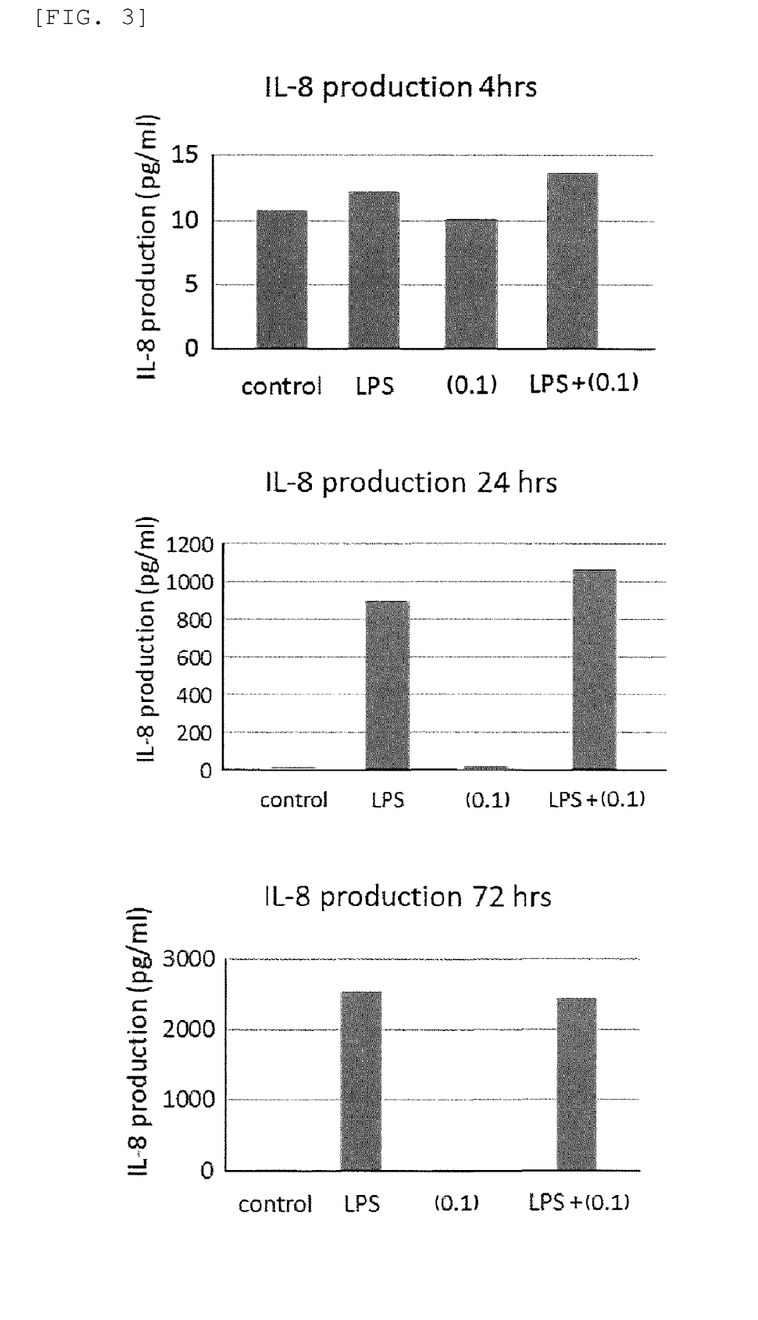
FIG. 3 graphically illustrates how the IL-8 production varies depending on time after the application (administration) of the pharmaceutical preparation obtained in the example.

The results demonstrate that, as compared with the comparative example using LPS alone, the example using the mixture (2) gave high IL-8 productions 4 hours and 24 hours after the application, but thereafter tended to have a decreasing IL-8 production, and gave a low IL-8 production 72 hours after the application (see FIG. 3).

Time-Dependent Change of IL-8 Gene Expression

The mixture (2) was applied to gingival fibroblasts (clinical sample (healthy gingiva); passage number: 7 to 10 passages), and the IL-8 production was measured 4 hours, 8 hours, and 24 hours after the application, where the mixture (2) is the mixture of the pharmaceutical preparation obtained in Example 2 and *P. gingivalis*-derived LPS (concentration: 1.0 μg/mL). Instead of the mixture (2), the application of LPS alone gave a comparative example, the application of the pharmaceutical preparation obtained in Example 2 alone gave a referential example (indicated as "(0.1)" in FIG. 4), and the application of water alone gave a control. The IL-8 gene expression was determined by real-time polymerase chain reaction (PCR) technique.

Figure 4:
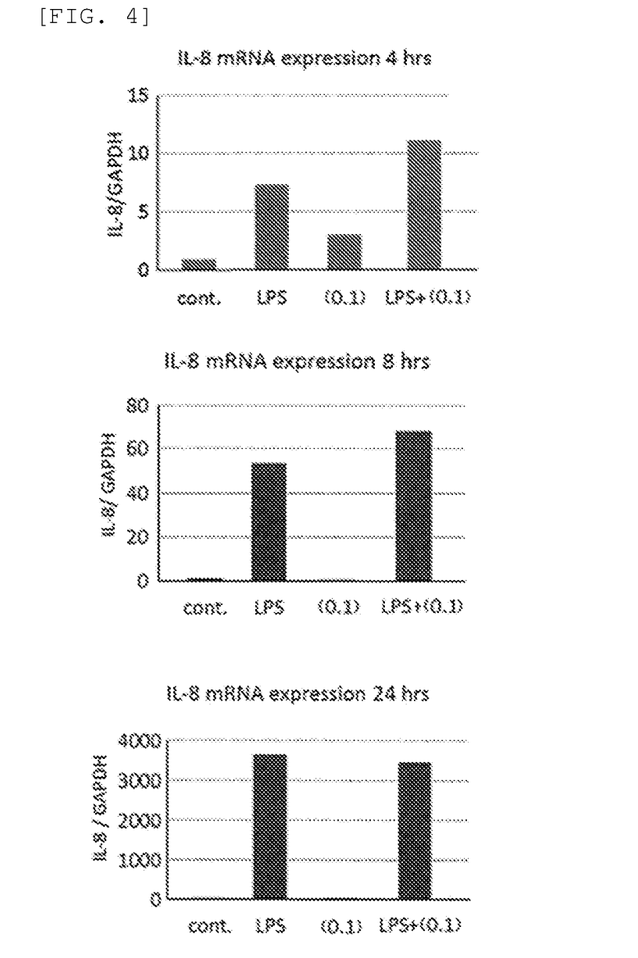
FIG. 4 graphically illustrates how the IL-8 gene expression level varies depending on time after the application of the pharmaceutical preparation obtained in the example.

The results demonstrate that, as compared with the comparative example using LPS alone, the example using the mixture (2) had high IL-8 gene expression levels 4 hours and 8 hours after the application, but thereafter tended to give decreasing IL-8 gene expression levels, and gave a low IL-8 gene expression level 24 hours after the application (see FIG. 4).

These results demonstrate that the wound repair promoter according to the present invention efficaciously increases the IL-8 production temporarily in gingival fibroblasts that have undergone LPS stimulation, terminates inflammation to terminate at an early stage, and shortens the time necessary for wound healing.

Example 6

Mouse fetus-derived fibroblasts were spread or inoculated in a 10% FCS-containing Dulbecco's modified Eagle medium (DMEM) and cultured for 24 hours. The 10% FCS-containing DMEM was then removed, and a fresh DMEM devoid of FCS was added, followed by cultivation for further 24 hours. Next, the DMEM containing the cells was combined with Nahlsgen or D-AP6 obtained in Preparation Example 1 to a concentration of 10 μg/mL, cultured for 5 hours, further combined with TGF-β, and cultured for further 5 hours. After the cultivation, RNAs or proteins were recovered, and the quantities of MMP3, MMP9, MMP13, FGF, TGF-β, amphiregulin, PDLIM2, and hyaluronic acid (HSA2) were determined using the real-time PCR technique.

Figure 5:
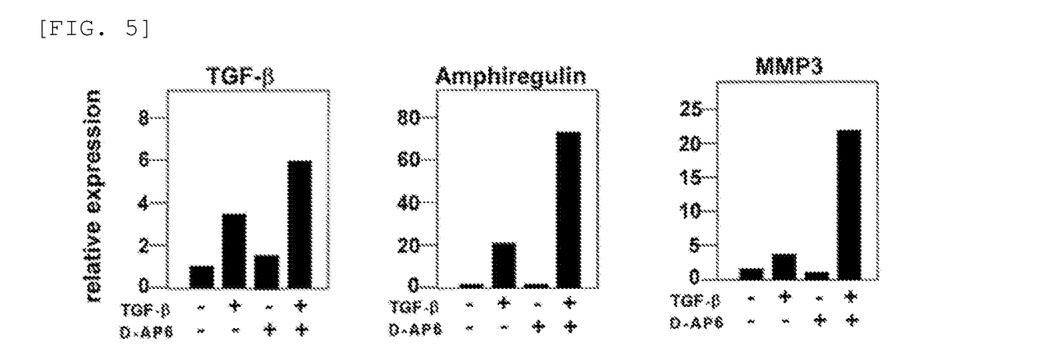
FIG. 5 graphically illustrates expression levels of TGF-β, amphiregulin, and MMP3 after the application of one or both of a pharmaceutical preparation (D-AP6) obtained in an example and TGF-β, where the ordinate indicates a relative expression determined while defining each gene expression in the absence of both TGF-β and D-AP6 as 1.

As a result, the addition of TGF-β alone increased the expression of MMP3, MMP9, MMP13, FGF, TGF-β, amphiregulin, and hyaluronic acid, but the addition of Nahlsgen or D-AP6 alone caused approximately no change in the expression levels. However, the addition of both TGF-β and Nahlsgen, or the addition of both TGF-β and D-AP6 significantly increased the expression levels as compared with the addition of TGF-β alone (see FIGS. 5, 6, and 7).

These results demonstrate as follows. The wound repair promoter according to the present invention, when applied to a wound site, coordinates with TGF-β, because such a wound causes TGF-β to be locally produced. This significantly accelerates the expressions of genes efficacious for a higher wound healing rate, and increases factors efficacious for a higher wound healing rate. Thus, the wound repair promoter increases the wound healing rate.

Figure 6:
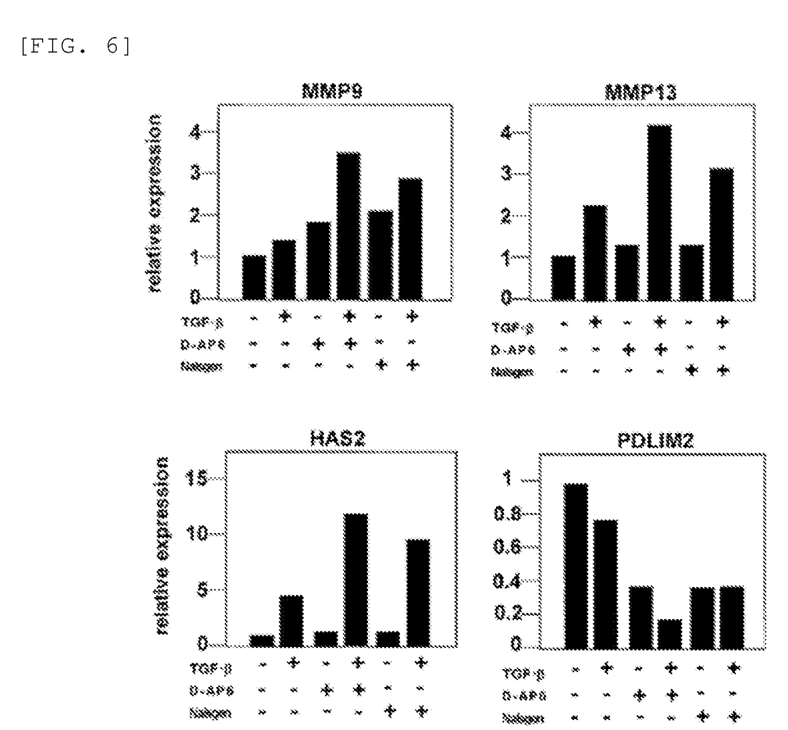
FIG. 6 graphically illustrates expression levels of MMP9, MMP13, hyaluronan synthase 2 (HAS2), and PDLIM2 after the application of one or both of D-AP6 and TGF-β, or after the application of one or both of Nahlsgen and TGF-β, where the ordinate indicates a relative expression determined while defining each gene expression in the absence of all of TGF-β, D-AP6, and Nahlsgen as 1.
Figure 7:
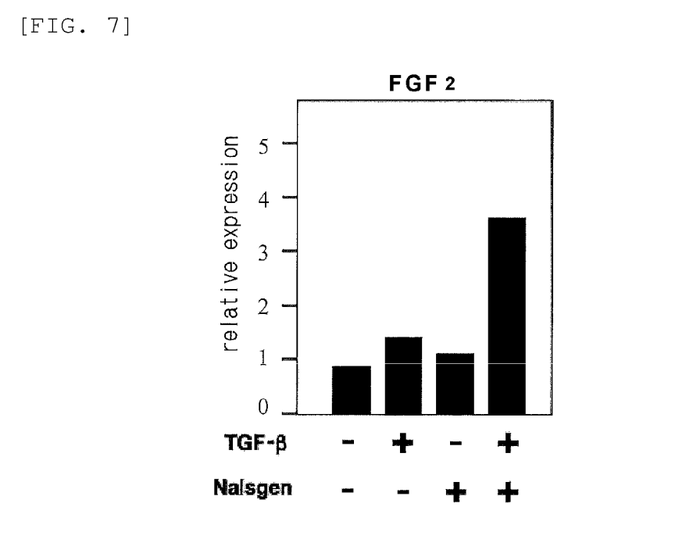
FIG. 7 is a graph illustrating the FGF2 expression after the application of one or both of Nahlsgen and TGF-β, where the ordinate indicates a relative FGF2 expression determined while defining the expression in the absence of both TGF-β and Nahlsgen as 1.

The addition of Nahlsgen or D-AP6 reduced PDLIM2 gene expression (see FIG. 6).

PDLIM2 inhibits or reduces differentiation from fibroblasts to myofibroblasts, restrains excessive acceleration of the wound healing rate, and reduces contraction and fibrosis of the wound site.

These demonstrate that the wound healing promoter (wound repair promoter) according to the present invention restrains PDLIM2, and, as a result, promotes wound healing (wound repair in fibroblasts-containing tissues, in particular, wound repair in dermis).

Example 7

Nahlsgen was diluted with water to give a pharmaceutical preparation (6) (concentration: 0.005%).

The pharmaceutical preparation (6) was administered as drops to the eyes of a domestic dog affected by conjunctivitis, and 30 minutes later an antibiotic (cefmenoxime hydrochloride 0.5%) was administered as drops to the eyes. This process was repeated twice a day for 5 days. This allowed the dog to have a transparent surface, which had been clouded, at the center part of the eyes and to have decreased redness and significantly reduced pus and eye mucus.

The domestic dog had suffered from signs of dry eye syndrome and often undergone conjunctivitis resulting from bacterial infection. Before the initiation of the dropwise administration (instillation) of the pharmaceutical preparation (6), the antibiotic had been continuously administered by instillation twice a day for one year or longer, but failed to enjoy curative effects, and had suffered from clouded eyes at the central part thereof due to white pus and a large amount of eye mucus.

These results verify that the wound repair promoter according to the present invention initially promotes ocular mucosal wound repair to improve ocular mucosal conditions, and, when combined with an antibiotic at this stage, allows the antibiotic to significantly exhibit antimicrobial effects, and provides high curative effects.

As a summary of the above description, the configurations according to embodiments of the present invention, as well as variations thereof, will be listed below as appendices.

(1) A wound repair promoter including at least one active ingredient selected from the group consisting of compounds represented by Formula (1), salts of the compounds, and hydrates of the compounds or the salts.

(2) The wound repair promoter according to (1), wherein the compounds represented by Formula (1) are selected from compounds (including optical isomers) represented by Formulae (I-1) to (I-5).

(3) The wound repair promoter according to (1), wherein the compounds represented by Formula (1) are selected from compounds (including optical isomers) represented by Formulae (II-1) and (II-2).

(4) The wound repair promoter according to any one of (1) to (3), which is a mucosal wound repair promoter.

(5) The wound repair promoter according to any one of (1) to (3), which is a wound repair promoter for a tissue including a fibroblast.

(6) The wound repair promoter according to any one of (1) to (5), which is a pharmaceutical preparation for preventing or treating a periodontal disease.

(7) The wound repair promoter according to any one of (1) to (5), which is in the form of a substance selected from the group consisting of dentifrices, mouthwashes, mouth sprays, gargles, chewable tablets, troches or drops, tablets, candies, chewing gum, liniments, plasters or adhesive skin patches, nasal drops, and eye drops, where the substance includes at least one active ingredient selected from the group consisting of the compounds represented by Formula (1), salts of the compounds, and hydrates of the compounds or the salts.

(8) A substance selected from the group consisting of dentifrices, mouthwashes, mouth sprays, gargles, chewable tablets, troches or drops, tablets, candies, chewing gum, liniments, plasters or adhesive skin patches, nasal drops, and eye drops, the substance containing at least one ingredient selected from the group consisting of compounds represented by Formula (1), salts of the compounds, and hydrates of the compounds or the salts.

(9) A substance selected from the group consisting of dentifrices, mouthwashes, mouth sprays, gargles, chewable tablets, troches or drops, tablets, candies, chewing gum, liniments, plasters or adhesive skin patches, nasal drops, and eye drops, the substance containing at least one ingredient selected from the group consisting of compounds represented by Formula (1), salts of the compounds, and hydrates of the compounds or the salts in a content of 0.001 to 500 µg/mL.

(10) A substance selected from the group consisting of dentifrices, mouthwashes, mouth sprays, gargles, chewable tablets, troches or drops, tablets, candies, chewing gum, liniments, plasters or adhesive skin patches, nasal drops, and eye drops, the substance containing at least one ingredient (including an optical isomer) selected from the group consisting of compounds represented by Formula (I-1) to (I-5), (II-1), and (II-2), salts of the compounds, and hydrates of the compounds or the salts.

(11) A substance selected from the group consisting of dentifrices, mouthwashes, mouth sprays, gargles, chewable tablets, troches or drops, tablets, candies, chewing gum, liniments, plasters or adhesive skin patches, nasal drops, and eye drops, the substance containing at least one ingredient (including an optical isomer) selected from the group consisting of compounds represented by Formula (I-1) to (I-5), (II-1), and (II-2), salts of the compounds, and hydrates of the compounds or the salts in a content of 0.001 to 500 µg/mL.

(12) A pharmaceutical preparation containing at least one ingredient selected from the group consisting of compounds represented by Formula (1), salts of the compounds, and hydrates of the compounds or the salts, the pharmaceutical preparation being in the form of a paste, gel, liquid, milky lotion, cream, aerosol, or sprayable preparation.

(13) A pharmaceutical preparation containing at least one ingredient selected from the group consisting of compounds represented by Formula (1), salts of the compounds, and hydrates of the compounds or the salts in a content of 0.001 to 500 µg/mL, the pharmaceutical preparation being in the form of a paste, gel, liquid, milky lotion, cream, aerosol, or sprayable preparation.

(14) A pharmaceutical preparation containing at least one ingredient (including an optical isomer) selected from the group consisting of compounds represented by Formula (I-1) to (I-5), (II-1), and (II-2), salts of the compounds, and hydrates of the compounds or the salts, the pharmaceutical preparation being in the form of a paste, gel, liquid, milky lotion, cream, aerosol, or sprayable preparation.

(15) A pharmaceutical preparation containing at least one ingredient (including an optical isomer) selected from the group consisting of compounds represented by Formula (I-1) to (I-5), (II-1), and (II-2), salts of the compounds, and hydrates of the compounds or the salts in a content of 0.001 to 500 µg/mL, the pharmaceutical preparation being in the form of a paste, gel, liquid, milky lotion, cream, aerosol, or sprayable preparation.

(16) The wound repair promoter according to any one of (1) to (3), which is an ocular mucosal wound repair promoter.

(17) The wound repair promoter according to any one of (1) to (3), which is a conjunctival wound repair promoter.

(18) The wound repair promoter according to any one of (1) to (3), which is a corneal wound repair promoter.

The invention claimed is:
1. A method of treating a conjunctival wound, comprising administering a therapeutically effective amount of at least one active ingredient selected from the group consisting of compounds represented by Formula (1), salts of the compounds, and hydrates of the compounds or the salts, Formula (1) expressed as follows:

wherein $R^1$ and $R^2$ are each, identically or differently, selected from hydrogen and a hydrocarbon group optionally having one or more substituents selected from the group consisting of halogens, —COOR$^3$, —CONR$^3_2$, —COR$^3$, —CN, —NO$_2$, —NHCOR$^3$, —OR$^3$, —SR$^3$, —OCOR$^3$, —SO$_3$R$^3$, and —SO$_2$NR$^3_2$, where R$^3$ is, identically or differently in each occurrence, selected from hydrogen and an optionally substituted aliphatic hydrocarbon group, and n represents an integer of 1 or more, to a wound site in an eye.

2. A method of treating a corneal wound, comprising administering a therapeutically effective amount of at least one active ingredient selected from the group consisting of compounds represented by Formula (1), salts of the compounds, and hydrates of the compounds or the salts, Formula (1) expressed as follows:

(1)

wherein R$^1$ and R$^2$ are each, identically or differently, selected from hydrogen and a hydrocarbon group optionally having one or more substituents selected from the group consisting of halogens, —COORS, —CONR$^3_2$, —COR$^3$, —CN, —NO$_2$, —NHCOR$^3$, —OR$^3$, —SR$^3$, —OCOR$^3$, —SO$_3$R$^3$, and —SO$_2$NR$^3_2$, where R$^3$ is, identically or differently in each occurrence, selected from hydrogen and an optionally substituted aliphatic hydrocarbon group, and n represents an integer of 1 or more, to a wound site in an eye.

3. A method of preventing or treating periodontal disease, comprising administering a therapeutically effective amount of a pharmaceutical preparation comprising at least one active ingredient selected from the group consisting, of compounds represented by Formula (1), salts of the compounds, and hydrates of the compounds or the salts, Formula (1) expressed as follows:

(1)

wherein R$^1$ and R$^2$ are each, identically or differently, selected from hydrogen and a hydrocarbon group optionally having one or more substituents selected from the group consisting of halogens, —COOR$^3$, —CONR$^3_2$, —COR$^3$, —CN, —NO$_2$, —NHCOR$^3$, —OR$^3$, —SR$^3$, —OCOR$^3$, —SO$_3$R$^3$, and —SO$_2$NR$^3_2$, where R$^3$ is, identically or differently in each occurrence, selected from hydrogen and an optionally substituted aliphatic hydrocarbon group; and n represents an integer of 1 or more, to the mouth.

* * * * *